United States Patent
Burch et al.

(10) Patent No.: US 6,552,031 B1
(45) Date of Patent: Apr. 22, 2003

(54) SYNERGISTIC ANALGESIC COMBINATION OF OXYCODONE AND ROFECOXIB

(75) Inventors: Ronald M. Burch; Paul D. Goldenheim, both of Wilton; Richard S. Sackler, Greenwich, all of CT (US)

(73) Assignee: Euro-Celtique S.A., Luxembourg (LU)

(*) Notice: Subject to any disclaimer, the term of this patent is extended or adjusted under 35 U.S.C. 154(b) by 0 days.

(21) Appl. No.: 09/154,354

(22) Filed: Sep. 17, 1998

Related U.S. Application Data

(60) Provisional application No. 60/059,195, filed on Sep. 17, 1997.

(51) Int. Cl.[7] .................... A01N 43/42; A61K 31/44
(52) U.S. Cl. .................. 514/282; 514/445; 514/241; 514/242; 514/252; 514/267; 514/359; 514/362; 514/363; 514/310; 514/365; 514/372; 514/374; 514/378; 514/383; 514/451; 514/444; 514/473; 546/18; 549/205; 549/323
(58) Field of Search ............... 514/241, 242, 514/252, 267, 359, 369, 363, 310, 365, 372, 374, 378, 383, 451, 444, 473; 546/18; 549/205, 323

(56) References Cited

U.S. PATENT DOCUMENTS

| | | | |
|---|---|---|---|
| 3,800,041 A | 3/1974 | Miller et al. | 424/273 |
| 4,322,427 A | 3/1982 | Buyniski et al. | 424/260 |
| 4,338,324 A | 6/1982 | Gardocki | 424/266 |
| 4,404,210 A | 9/1983 | Schmidt | 424/260 |
| 4,407,804 A | 10/1983 | Schmidt | 424/260 |
| 4,407,805 A | 10/1983 | Schmidt | 424/260 |
| 4,464,376 A | 8/1984 | Sunshine et al. | 424/253 |
| 4,486,436 A | 12/1984 | Sunshine et al. | 424/253 |
| 4,489,080 A | 12/1984 | Lomen | 424/260 |
| 4,567,183 A * | 1/1986 | Sunshine et al. | 514/264 |
| 4,569,937 A | 2/1986 | Baker et al. | 514/282 |
| 4,571,400 A | 2/1986 | Arnold | 514/282 |
| 4,587,252 A | 5/1986 | Arnold | 514/282 |
| 4,619,934 A | 10/1986 | Sunshine et al. | 514/277 |
| 4,690,927 A | 9/1987 | Voss et al. | 514/282 |
| 4,839,176 A | 6/1989 | Pahkhania et al. | 424/465 |
| 4,844,907 A | 7/1989 | Elger et al. | 424/465 |
| 4,927,854 A | 5/1990 | Sunshine et al. | 514/570 |
| 5,164,398 A | 11/1992 | Sims et al. | 514/282 |
| 5,190,947 A | 3/1993 | Riess et al. | 514/282 |
| 5,240,694 A | 8/1993 | Gwaltney, Jr. | 424/45 |
| 5,409,944 A | 4/1995 | Black et al. | 514/359 |
| 5,436,265 A | 7/1995 | Black et al. | 514/420 |
| 5,458,879 A | 10/1995 | Singh et al. | 424/400 |
| 5,474,995 A | 12/1995 | Ducharme et al. | 514/241 |
| 5,510,368 A | 4/1996 | Lau et al. | 514/419 |
| 5,516,803 A | 5/1996 | Raffa | 514/570 |
| 5,521,213 A | 5/1996 | Prasit et al. | 514/443 |
| 5,550,142 A * | 8/1996 | Ducharme et al. | 514/365 |
| 5,552,422 A | 9/1996 | Gauthier et al. | 514/368 |
| 5,604,253 A | 2/1997 | Lau et al. | 514/415 |
| 5,604,260 A | 2/1997 | Guay et al. | 514/605 |
| 5,639,780 A | 6/1997 | Lau et al. | 514/419 |
| 5,691,374 A | 11/1997 | Black et al. | 514/473 |
| 5,789,413 A | 8/1998 | Black et al. | 514/255 |
| 5,840,731 A | 11/1998 | Mayer et al. | 514/289 |
| 5,843,468 A | 12/1998 | Burkoth et al. | 424/448 |
| 5,859,257 A * | 1/1999 | Talley | 548/247 |
| 5,861,419 A | 1/1999 | Dube et al. | 514/334 |
| 5,863,922 A | 1/1999 | Mayer et al. | 514/270 |
| 5,869,498 A | 2/1999 | Mayer et al. | 514/282 |

FOREIGN PATENT DOCUMENTS

| | | | |
|---|---|---|---|
| AU | 0734275 | 11/1997 | C07D/261/08 |
| CA | 2023349 | 2/1991 | A61K/31/44 |
| CA | 2081604 | 5/1995 | A61K/31/135 |
| EP | 0068838 | 6/1982 | A61K/31/485 |
| EP | 0274845 | 7/1988 | A61K/31/19 |
| EP | 0388125 | 9/1990 | A61K/31/485 |
| EP | 0654263 | 5/1995 | A61K/31/135 |
| WO | 9717978 | 5/1997 | A61K/33/00 |
| WO | 9725988 | 7/1997 | A61K/31/495 |
| WO | 9732857 | 9/1997 | C07D/241/104 |
| WO | 9907413 | 2/1999 | |
| WO | 9932119 | 7/1999 | |

OTHER PUBLICATIONS

Rorarius et al., "Non–Steroidal Anti–Inflammatory Drugs for PostOperative Pain Relief," Curr. Opin. In Anaesthesiology, 7, 358–362.), 1994.*

Hanses et al. "Pharmacokinetics and Drug input Characteristics for a Diclofenac–Codeine Phosphate Combination Following Oral and Rectal Administration," Arzneim.–Forsch./Drug Res., 46(1), Nr. 1, 57–63., 1996.*

Merck Index, Twelfth Edition, Merck & Co. Publishers, p. 1194., 1996.*

Goodman and Gilman's: The Paramaceutical Basis of Therapeutics, "Chapter 22:Opioid Analgesics and Antagonists", MacMillan Publishing Co., Inc., pp. 494–497, esp. Table 22–1, p. 496., 1980.*

*Effect of meloxicam on postoperative pain after abdominal hysterectomy*, J.P. Thompson et al. *British Journal of Anaesthesia* 84 (2) 151–4 (2000).

*Intrathecal cyclooxygenase inhibitor admistration attenuates morphine antinociceptive tolerance in rats*, C.S. Wong et al., *British Journal of Anaesthesia* 85 (5) 747–51 (2000).

(List continued on next page.)

Primary Examiner—Bennett Celsa
(74) Attorney, Agent, or Firm—Davidson, Davidson & Kappel, LLC

(57) ABSTRACT

Disclosed is a pharmaceutical composition, comprising a combination of a dose of rofecoxib or a pharmaceutically acceptable salt thereof and a dose of oxcodone or a pharmaceutically acceptable salt thereof, said combination in an amount sufficient to provide an analgesic effect in a human patient. Also disclosed is a method of effectively treating pain in humans or other mammals, comprising administering to the patient a combination of a dose of rofecoxib or a pharmaceutically acceptable salt thereof and a dose of oxycodone or a pharmaceutically acceptable salt thereof such that the dosing interval of the rofecoxib overlaps with the dosing interval of the oxycodone, said combination in an amount sufficient to provide an analgesic effect in a human patient.

19 Claims, 3 Drawing Sheets

OTHER PUBLICATIONS

*Cyclooxygenase inhibitors increase morphine effects on mesolimbic dopamine neurons*, M. Melis, et al. *Eur. J. Pharmacology* 387 (1) R1–R3 (2000).

Synergistic antiallodynic effects of spinal morphine with ketorolac and selective COX1– and COX2–inhibitors in nerve–injured rats, J.M. Lashbrook, et al. *Pain* 82 (1) 65–72 (1999).

Enhancement of opioid inhibiton of gaba–ergic synaptic transmission by cyclo–oxygenase inhibitors in rat periaqueductal grey neurones, Vaughn et al. *British Journal of Pharmacology* 123(8) 1479–81 (1998).

*Anti–inflammatory Drugs and Their Mechanism of Action* J.R. Vane, et al. Inflamm. Res. 47, Supplement 2 (1998).

Differential Inhibition of Cyclooxygenase–1 (COX–1) and –2 (COX) By NSAIDS: Consequences on Anti–Inflammatory Activity Versus Gastric and Renal Safety, M. Pairet, et al., Inflammopharmacology 4; 61–70, (1996).

Differential effects of inhibitors of cyclooxygenase (cyclooxygenase 1 and cyclooxygenase 2) in acute inflammation, Derek W. Gilroy, et al. Europeam J. Pharm 355 pp. 211–217, (1998).

Cyclooxygenases 1 and 2, J.R. Vane, et al. Annu. Rev. Pharmacol. Toxicol. 38: 97–121, (1998).

Analysis of the effects of cyclooxygenase (COX)–1 and COX–2 in spinal nociceptive transmission using indomethacin, a non–selective COX inhibitor, and NS–398, a COX–2 selective inhibitor, Tatsuo Yamamoto, et al. Brain Research 739:104–110, (1996).

Comparative Analgesic Efficacy of Nimesulide and Diclofenac Gels after Topical Application on the Skin, S. Sengupta, et al., Skin Pharmacol. and Applied Skin Phys. 11:273–278, (1998).

Carrageenan–induced hyperalgesia is associated with increased cyclo–oxygenase–2 expression in spinal cord, Cartiona Hay and Jacqueline de Belleroche, NeuroReport 8, 1249–1251, (1997).

The Mechanisms of Action in NSAIDs in Analgesia, Jeremy N. Cashman, Drug 52 Supp. 5:13–23, (1996).

Differential effects of inhibition of isoforms of cyclooxygenase (COX–1, COX–2) in chronic inflammation, D.W. Gilroy, et al. Inflamm. Res. 47: 79–85, (1998).

Constitutive Cyclooxygenase (COX–1) and Inducible Cyclooxygenase (COX–2): Rationale for Selective Inhibition and Progress to Date, Don E. Griswold and Jerry L. Adams, Medicinal Research Reviews, vol. 16, No. 2, pp. 181–206, (1996).

Cyclooxygenase in biology and disease, Raymond N. Dubois, et al., FASEB J. vol. 12 pp. 1063–1073 (1998).

Pharmacology of Meloxicam, A new Non–Steroidal Anti–Inflammatory Drug with an Improved Safety Profile Through Preferential Inhibition of COX–2, G. Engelhardt, British J. Rheumatology, 35 (supp 1):4–12, (1996).

Cyclooxygenase 1 Contributes to Inflammatory Responses in Rats and Mice: Implications for Gastrointestinal Toxicity, John L. Wallace, et al. Gastroenterology, 115:101–109 (1998).

Distinct isoforms (COX–1 and COX–2) of cyclooxygenase: possible physiological and therapeutic implications, M. Pairet and G. Engelhardt, Fundam. Clin. Pharmacol. 10:1–15, (1996).

Involvement of Prostaglandins Produced by Cyclooxygenase–1 in Murine Viscernonociception Induced by Phenylquinone, Hidenobu Kusuhara, et al. Prostaglandins 55:43–49, (1998).

Effect of COX–1 and COX–2 Inhibition on Induction and Maintenance of Carrageenan–Evoked Thermal Hyperalgesia in Rats. D. Dirig, et al. J Pharmacol. and Experimental Therapeutics vol. 285, No. 3, pp. 1031–1038.

Pharmacokinetics and Drug Input Characteristics for a Diclofenac–Codeine Phosphate Combination Following Oral and Rectal Administration A. Hansen, et al. Arzneim.–Forsch./Drug Res. 46 (I), 57–63 (1996).

Comparison of a Standard Ibuprofen Treatment Regimen with a New Ibuprofen/Paracetamol/Codeine Combination in Chronic Osteo–arthritis G. K. Vlok, et al. Univ. Stellenbosch and Tygerberg Hospital, Dept. Orthopaedic Surg. pp. 3–6, (1987).

*Pharmacokinetics and Drug Input Characteristics for a Diclofenac–Codeine Phosphate Combination Following Oral and Rectal Administration* A. Hansen, et al., Arzneim.–Forsch./Drug Res. 46 (I), 57–63 (1996).

*Comparison of a Standard Ibuprofen Treatment Regimen with a New Ibuprofen/Paracetamol/Codeine Combination in Chronic Osteo–arthritis* G. K. Vlok, et al. Univ. Stellenbosch and Tygerberg Hospital, Dept. Orthopaedic Surg. pp. 3–6, (1987).

Dray et al. New Pharmacological Strategies for Pain Relief. *Annual Review of Pharmacology & Toxicology*, 36, pp. 253–280. (1996).

Brasseur. L. Revue des therapeutiques pharmacolgoiques actuelles de la douleur. *Drugs*, 53 Suppl 2, pp. 10–17. (1997).

Rang et al. New molecules in analgesia. *British Journal of Anesthesia*, 75, pp. 145–156 (1995).

Beaver, WT. Combination Analgesics. *American Journal of Medicine*, 77 (Suppl 3A), pp. 38–53. (1984).

Beaver, WT. Chapter 29: Nonsterodial Antiinflammatory Analgesics and Their Combinations with Opioids. In *Evaluation and Treatment of Chronic Pain*, $2^{nd}$ ed., William & Wilkins pp. 363–383. (1992).

Goodman & Gilman's. The Pharmacological Basis of Therapeutics, $9^{th}$ Edition. McGraw–Hill, New York, pp. 535 and 551–552.

Picard et al. Ketorolac potentiates morphine in postoperative patient–controlled analgesia. *Pain*, 73, 3 pp. 401–406. (1997).

Etches et al., Continuous Intravenous Administration of Ketorolac Reduces Pain and Morphine Consumption After Total Hip or Knee Arthroplasty. *Anesthesia & Analgesia*, 81 (6), pp. 1175–1180. (1995).

Kaasalainer et al. Developments in the treatment of cancer pain in Finland: The third nation–wide survey. *Pain*, 70, 2–3, pp. 175–183. (1997).

Sunshine et al. Analgesic Efficacy of a Hydrocodone with Ibuprofen Combination Compared with Ibuprofen Alone for the Treatment of Acute Postoperative Pain. *Journal of Clinical Pharmacolology*, 37 (10), pp. 908–915. (1997).

Insel. Chapter 27: Analgesic–Antipyretic and Anti–inflammatory Agents. In Hardman, ed., *Goodman & Gilman's The Pharmacological Basis of Therapeutics*, $9^{th}$ Edition. McGraw–Hill, New York, pp. 654–655. (1996).

Polisson. Non–steroidal Anti–inflammatory Drugs: Practical and Theoretical Consideration in Their Selection. *The American Journal of Medicine*, 100 (Suppl 2A), pp. 2A–31S –2A–36S. (1996).

Vane, J. Towards a better asprin. *Nature*, 367, pp. 215–216. (1994).

Simon, L. S. Nonsteroidal Antiinflammatory Drugs and Their Effects: The Importance of Cox 'Selectivity'. *Journal of Clinical Rheumatology*, 2 (3), pp. 135–140. (1996).

Van Ryn et al. Selective cycloocygenase–2 inhibitors: pharmacology, clinical effects, and therapeutic potential. *Expert Opinion On Investigational Drugs*, pp. 609–614. (1997).

Vane et al. New insights into the mode of action of anti–inflammatory drugs. *Inflammation Research*. 44, (No. 1), pp. 1–10 (1995).

Engelhardt. Meloxicam: A Preferential Inhibitor of COX–2. *British Journal of Rheumatology*. 34, Abstract Suppl. 1, p. 48, (1995). Abstract.

Lane, N. E. Pain Management in Osteoarthritis: The Role of COX–2 Inhibitors. *Journal of Rheumatology*, vol. 24, Suppl 49, pp. 20–24. (1997).

Boyce et al. L–745, 337: A Selective Inhibitor of Cyclooxygenase–2 Elicits Antinociception But Not Gastric Ulceration in Rats. *Neuropharmacology* vol. 33, pp. 1609–1611. (1994).

Donelly et al. COX–II Inhibitors –a new generation of safer NSAIDS? *Alimentary Pharmacology and Therapeutics*, 11, 2, pp. 227–236. (1997).

Wallace, J. L. Nonsteroidal Anti–inflammatory Drugs and Gastroenteropathy: The Second Hunderd Years. *Gastroenterology*, 112, 3, pp. 1000–1016. (1997).

Robinson, D. R. Regulation of Prostaglandin Synthesis by Antiinflammatory Drugs. *J. Rheumatoloty*, 24, Suppl. 47, pp. 32–39. (1997).

Tannenbaum et al. An Evidence–Based Approach to Prescribing NSAIDS in Muscoskeletal Disease: A Canadian Consensus. *Canadian Medical Association Journal*, 155, 1, pp. 77–88. (1996).

Mehlisch et al. Analgesic Efficacy and Plasma Levels of a Highly Selective Inhibitor of COX–2 (SC–58635, SC) in Patients with Postsurgical Dental Pain. *Journal of Clinical Pharmacology*, 37, 9, 863. (1997). Abstract.

Dammann. Selective COX–2 Inhibition: Its Relevance for NSAID–Gastrointesinal Toxicity. *Gut*, 39, Suppl. 3, A151. (1996).

Penning et al. Synthesis and Biological Evaluation of the 1, 5 –diarylpyrazole class of cylooxygenase–2 Inhibitors: Identification of 4–[5–(4–methylphenyl)–3–(trifluoromethyl)–1H–pyrazol–1–yl]benzenesulfonamide (SC–58635, Celecoxib). *Journal Of Medicinal Chemistry*, 40(9), 1347–65. (1997).

Lipsky et al. Outcome of Specific COX–2 Inhibition in Rheumatoid Arthritis. *Journal Of Rheumatology*, 24 Suppl 49, pp. 9–14. (1997).

* cited by examiner

SYNERGISTIC ANALGESIC COMBINATION OF OXYCODONE AND ROFECOXIB

This application claims the benefit of U.S. Provisional Application Ser. No. 60/059,195, filed Sep. 17, 1997.

FIELD OF THE INVENTION

The invention relates to analgesic pharmaceutical compositions containing an opioid analgesic and a cyclooxygenase-2 (COX-2) inhibitor. The invention also relates to methods of treating pain comprising administering such pharmaceutical compositions to human patients.

BACKGROUND OF THE INVENTION

There is a continuing need for analgesic medications able to provide high efficacy pain relief while reducing the possibility of undesirable effects. Non-steroidal antiinflammatory drugs ("NSAID'S"), including compounds such as ibuprofen, ketoprofen and diclofenac, have antiinflammatory actions and are effective on pain associated with the release of prostaglandins and other mediators of inflammation. For example, diclofenac is considered to be extremely potent and effective as an analgesic and antiinflammatory agent. Diclofenac is approved in the United States for the long-term symptomatic treatment of rheumatoid arthritis, osteoarthritis and ankylosing spondylitis. It is also considered to be useful for the short-term treatment of acute musculoskeletal injury, acute painful shoulder, postoperative pain and dysmenorrhea. However, NSAID'S such as diclofenac produce side effects in about 20% of patients that require cessation of medication. Side effects include, for example, gastrointestinal bleeding and the abnormal elevation of liver enzymes.

The opioids are a group of drugs, both natural and synthetic, that are employed primarily as centrally-acting analgesics and are opium or morphine-like in their properties (Gilman et al., 1980, *GOODMAN AND GILMAN'S. THE PHARMACOLOGICAL BASIS OF THERAPEUTICS*, Chapter 24:494–534, Pub. Pergamon Press; hereby incorporated by reference). The opioids include morphine and morphine-like homologs, including, e.g., the semisynthetic derivatives codeine (methylmorphine) and hydrocodone (dihydrocodeinone) among many other such derivatives. Morphine and related opioids exhibit agonist activity at central nervous system or CNS (referring to the brain and spinal cord) $\mu$ (mu) opioid receptors as well as showing affinity for the $\delta$ and $\kappa$ opioid receptors, to produce a range of effects including analgesia, drowsiness, changes in mood and mental clouding. In addition to potent analgesic effects, the morphine-related opioids may also cause a number of undesirable effects, including, for example, respiratory depression, nausea, vomiting, dizziness, mental clouding, dysphoria, pruritus, constipation, increased biliary tract pressure, urinary retention and hypotension. The development of tolerance to the opioid drugs and the risk of chemical dependence and abuse for these drugs is another undesirable effect.

Morphine, which has been considered the prototypic opioid analgesic, has been available in many dosage forms, including immediate release oral dosage forms, and more recently, formulated into 12 hour controlled release formulations (e.g., MS Contin® tablets, commercially available from Purdue Frederick Company). Other opioid analgesics have been available as immediate release oral dosage forms, such as hydromorphone (e.g., Dilaudid®, commercially available from Knoll Pharmaceuticals). More recently, another controlled release opioid analgesic, oxycodone, has become available (OxyContin®, commercially available from Purdue Pharma). There are, of course, many other oral formulations of immediate release and sustained release opioids which are commercially available throughout the world.

Prior publications report that analgesic potency may be improved while reducing undesirable effects by combining an opioid with an NSAID or an analgesic such as acetylsalicylic acid or acetaminophen, in such a way as to obtain a synergistic analgesic effect allowing for a reduction in the total dose of both the NSAID and analgesic. For example, U.S. Pat. No. 4,569,937, issued to Baker et al. on Feb. 11, 1986, describes a combination of oxycodone with ibuprofen in a ratio of oxycodone/ibuprofen from 1:6 to about 1:400. U.S. Pat. No. 4,690,927, issued to Voss et al. on Sep. 1, 1987, describes a combination of the NSAID diclofenac and codeine in a weight ratio of diclofenac to codeine of about 1:1 to about 3:1. U.S. Pat. No. 5,190,947, issued to Riess et al. on Mar. 2, 1993, describes a diclofenac-codeine salt ([2-[2,6-dichlorophenyl)-amino]-phenyl]-acetic acid). U.S. Pat. No. 4,844,907, issued to Elger et al. on Jul. 4, 1989, describes a multiphase tablet combining a narcotic analgesic phase and an NSAID phase in separate layers. U.S. Pat. No. 4,587,252, issued to Arnold et al. on May 6, 1986, describes a process for treating pain using a combination of hydrocodone and ibuprofen.

Non-steroidal, anti-inflammatory drugs (NSAID'S) exert most of their anti-inflammatory, analgesic and antipyretic activity and inhibit hormone-induced uterine contractions and certain types of cancer growth through inhibition of prostaglandin G/H synthase, also known as cyclooxygenase.

Fatty acid cyclooxygenase (COX) was described as the source of prostaglandins, thromboxanes, and a variety of other arachidonic acid-, and higher desaturated fatty acid-derived biologically active hydroxylated metabolites. Beginning in the late 1960's, B. Sammuelsson, S. Bergstrom and their colleagues discovered the biological activity and elucidated the structures of the products of cyclooxygenase. In the late 1960's and early 1970's, J. Vane discovered that aspirin and other NSAIDs exert their major biological activities by inhibiting cyclooxygenase. COX is directly responsible for the formation of PGG and PGH and these serve as the intermediates in the synthesis of PGD, PGE, PGF, PGI, and TXA. By the late 1970's and early 1980's, it was appreciated that many hormones and other biologically active agents could regulate the cellular activity of COX. At first, it was assumed that COX induction was the simple result of oxidative inactivation of COX, which happens after only a few substrate turnovers. This is common among enzymes that incorporate molecular oxygen into their substrates— the oxygen rapidly degrades the enzyme. Such enzymes are sometimes referred to as suicide enzymes. In response to the rapid (within seconds) inactivation of cyclooxygenase, its message is transcribed, and the enzyme is rapidly induced to replace that lost due to catalysis. It was noticed by several groups that cyclooxygenase was induced to a much greated degree than necessary to replace the lost enzyme. Using an oligonucleotide directed to the cloned COX-1 enzyme, a second band was identified on Northern blots under low stringency. This gene was cloned and identified as a second COX enzyme, named COX-2, and was found to be largely absent from many cells under basal conditions but rapidly induced by several cytokines and neurotransmitters. The expression of this enzyme was found to be largely responsible for the previously-observed excess COX activity in activated cells. The genes for COX-1 and COX-2 are distinct, with the gene for COX-1 being 22 kb and the message size 2.8 kb whereas the gene for COX-2 is 8.3 kb and the message size 4.1 kb. Whereas the COX-1 promoter does not contain recognized transcription factor binding sites, the COX-2 promoter contains sites for NF-κB, AP-2, NF-IL-6 and glucocorticoids (H. R. Herschman, Canc. Metas. Rev. 13: 256, 1994). There are some differences in the active sites of the enzymes. Aspirin inhibits the cyclooxygenase activity of COX-1 but leaves intact its peroxidase activity, whereas aspirin converts COX-2 from a cyclooxygenase to a 15-lipoxygenase (E. A. Meade et al, J. Biol. Chem. 268: 6610, 1993).

It has been proposed that the COX-1 is responsible, in many cells for endogenous basal release of prostaglandins and is important in the physiological functions of prostaglandins which include the maintenance of gastrointestinal integrity and renal blood flow. Inhibition of COX-1 causes a number of side effects including inhibition of platelet aggregation associated with disorders of coagulation, and gastrointestinal toxicity with the possibility of ulcerations and of hemorrhage. It is believed that the gastrointestinal toxicity is due to a decrease in the biosynthesis of prostaglandins which are cytoprotective of the gastric mucosa.

A high incidence of side effects has historically been associated with chronic use of classic cyclooxygenase inhibitors, all of which are about equipotent for COX-1 or COX-2, or which are COX-1-selective. While renal toxicity occurs, it usually becomes evident in patients who are already exhibit renal insufficiency (D. Kleinknecht, Sem. Nephrol. 15: 228, 1995). By far, the most prevalent and morbid toxicity is gastrointestinal. Even with relatively nontoxic drugs such as piroxicam, up to 4% of patients experience gross bleeding and ulcertaion (M. J. S. Langman et al, Lancet 343: 1075, 1994). In the United States, it is estimated that some 2000 patients with rheumatoid arthritis and 20,000 patients with osteoarthritis die each year due to gastrointestinal side effects related to the use of COX inhibitors. In the UK, about 30% of the annual 4000 peptic ulcer-related deaths are attributable to COX inhibitors (Scrip 2162, p.17). COX inhibitors cause gastrointestinal and renal toxicity due to the inhibition of synthesis of homeostatic prostaglandins responsible for epithelial mucus production and renal blood flow, respectively.

The second form of cyclooxygenase, COX-2, is rapidly and readily inducible by a number of agents including mitogens, endotoxins, hormones, cytokines and growth factors.

It has been proposed that COX-2 is mainly responsible for the pathological effects of prostaglandins, which arise when rapid induction of COX-2 occurs in response to such agents as inflammatory agents, hormones, growth factors, and cytokines. A selective inhibitor of COX-2 therefore would have anti-inflammatory, antipyretic and analgesic properties similar to those of a conventional non-steroidal anti-inflammatory drug (NSAID). Additionally, a COX-2 inhibitor would inhibit hormone-induced uterine contractions and have potential anti-cancer effects. A COX-2 inhibitor would have advantages over NSAID'S such as a diminished ability to induce some of the mechanism-based side effects. Moreover, it is believed that COX-2 inhibitors have a reduced potential for gastrointestinal toxicity, a reduced potential for renal side effects, a reduced effect on bleeding times and a lessened ability to induce asthma attacks in aspirin-sensitive asthmatic subjects.

Thus, compounds with high specificity for COX-2 over COX -1, may be useful as alternatives to conventional NSAID'S. This is particularly the case when NSAID use is contra-indicated, such as in patients with peptic ulcers, gastritis, regional enteritis, ulcerative colitis, diverticulitis or with a recurrent history of gastrointestinal lesions; GI bleeding, coagulation disorders including anemia, hypoprothrombinemia, haemophelia or other bleeding problems; kidney disease, and patients about to undergo surgery or taking anticoagulants.

Once it became clear that COX-1 but not COX-2 is responsible for gastrointestinal epithelial prostaglandin production and a major contributor to renal prostaglandin synthesis, the search for selective COX-2 inhibitors became extremely active. This led very quickly to the recognition that several COX inhibitors, including nimesulide and Dup-697, which were known to cause little or no gastrointestinal irritation, are COX-2-selective.

U.S. Pat. No. 5,409,944 (Black, et al.) describes certain novel alkane-sulfonamido-indanone derivatives useful for the treatment of pain, fever, inflammation, arthritis, cancer, and other disease states. Also discussed therein are compositions for the treatment of cyclooxygenase-2-mediated diseases comprising the therein-described novel alkane-sulfonamidoindanone derivatives together with a pain reliever including acetaminophen or phenacetin; a potentiator including caffeine; an H2-antagonist, aluminium or magnesium hydroxide, simethicone, a decongestant including phenylephrine, phenylpropanolamine, pseudophedrine, oxymetazoline, epinephrine, naphazoline, xylonetazoline, propylhexedrine, or levo-desoxy ephedrine; an antitussive including codeine, hydrocodone, caramiphen, carbetapentane or dextromethorphan; a diuretic and/or a sedating or non-sedating antihistamine. While Black et al. mention the use of an antitussive dose of two opioid analgesics (codeine and hydrocodone), they do not describe or suggest the use of their COX-2 inhibitors with analgesically effective amounts of any opioid analgesics.

SUMMARY OF THE INVENTION

It is an object of the present invention to provide a method and pharmaceutical formulation (medicament) which allows for reduced plasma concentrations of an opioid analgesic, while still providing effective pain management.

It is a further object of the present invention to provide a method and pharmaceutical formulation (medicament) for effectively treating patients in pain with an opioid analgesic which achieves prolonged and effective pain management, while at the same time provides the opportunity to reduce side effects, dependence and tolerance which the patients may experience when subjected to prolonged treatment with an opioid.

It is yet a further object to provide a method and pharmaceutical formulation (medicament) for the effective treatment of pain in patients by augmenting the analgesic effect of a COX-2 inhibitor.

The invention is directed to the surprising synergy obtained via the administration of an opioid analgesic together with a COX-2 inhibitor.

The present invention is related in part to analgesic pharmaceutical compositions comprising a COX-2 inhibitor together with an opioid analgesic. The opioid analgesic and COX-2 inhibitor can be administered orally, via implant, parenterally, sublingually, rectally, topically, via inhalation, etc. In other embodiments of the invention, the COX-2 inhibitor can be administered separately from the opioid analgesic, as set forth in more detail below.

The invention allows for the use of lower doses of the opioid analgesic or the COX-2 inhibitor (referred to as "apparent one-way synergy" herein), or lower doses of both drugs (referred to as "two-way synergy" herein) than would normally be required when either drug is used alone. By using lower amounts of either or both drugs, the side effects associated with effective pain management in humans are significantly reduced.

In certain preferred embodiments, the invention is directed in part to synergistic combinations of a COX-2 inhibitor in an amount sufficient to render a therapeutic effect together with an opioid analgesic, such that an an analgesic effect is attained which is at least about 5 (and preferably at least about 10) times greater than that obtained with the dose of opioid analgesic alone, except for combinations of the COX-2 inhibitor with anti-tussive doses of hydrocodone or codeine. In certain embodiments, the synergistic combination provides an analgesic effect which is up to about 30–40 times greater than that obtained with the dose of opioid analgesic alone. In such embodiments, the synergistic combinations display what is referred to herein as an "apparent one-way synergy", meaning that the dose of COX-2 inhibitor synergistically potentiates the effect of the opioid analgesic, but the dose of opioid analgesic does not appear to significantly potentiate the effect of the COX-2 inhibitor. In certain embodiments, the combination is administered in a single dosage form. In other embodiments, the combination is administered separately, preferably concomitantly. In certain preferred embodiments, the synergism exhibited between the COX-2 inhibitor and the opioid analgesic is such that the dosage of opioid analgesic would be sub-therapeutic if administered without the dosage of COX-2 inhibitor. In other preferred embodiments, the present invention relates to a pharmaceutical composition comprising an analgesically effective dose of an opioid analgesic together with a dose of a COX-2 inhibitor effective to augment the analgesic effect of the opioid analgesic.

Although certain embodiments of the invention are directed to synergistic combinations of a COX-2 inhibitor together with an opioid analgesic, where there is an apparent "one-way synergism", it is believed that in actuality these combinations exhibit two-way synergism, meaning that the COX-2 inhibitor potentiates the effect of the opioid analgesic, and the opioid analgesic potentiates the effect of the COX-2 inhibitor. Thus, other embodiments of the invention relate to combinations of a COX-2 inhibitor and an opioid analgesic where the dose of each drug is reduced due to the synergism demonstrated between the drugs, and the analgesia derived from the combination of drugs in reduced doses is surprisingly enhanced. The two-way synergism is not always readily apparent in actual dosages due to the potency ratio of the opioid analgesic to the COX-2 inhibitor (meaning that the opioid generally displays much greater relative analgesic potency).

In certain preferred embodiments, the invention is directed to pharmaceutical formulations comprising a COX-2 inhibitor in an amount sufficient to render a therapeutic effect together with a therapeutically effective or sub-therapeutic amount of an opioid analgesic selected from the group consisting of alfentanil, allylprodine, alphaprodine, anileridine, benzylmorphine, bezitramide, buprenorphine, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene fentanyl, heroin, hydromorphone, hydroxypethidine, isomethadone, ketobemidone, levallorphan, levorphanol, levophen-acylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, salts thereof, complexes thereof; mixtures of any of the foregoing, mixed mu-agonists/antagonists, mu-antagonist combinations salts or complexes thereof, and the like. In certain preferred embodiments, the opioid analgesic is a mu or kappa opioid agonist. In certain preferred embodiments, the invention is directed to pharmaceutical formulations comprising a COX-2 inhibitor in an amount sufficient to render a therapeutic effect together with a therapeutically effective or sub-therapeutic amount of an opioid analgesic selected from the group consisting of morphine, dihydrocodeine, hydromorphone, oxycodone, oxymorphone, salts thereof, and mixtures of any of the foregoing.

In certain preferred embodiments, the invention is directed to pharmaceutical formulations comprising a COX-2 inhibitor in an amount sufficient to render a therapeutic effect together with a dose of codeine which is analgetic if administered without the COX-2 inhibitor. Such a dose of codeine is preferably from about 30 to about 400 mg.

In certain preferred embodiments, the invention is directed to pharmaceutical formulations comprising a COX-2 inhibitor in an amount sufficient to render a therapeutic effect together with a dose of hydrocodone which is analgetic if administered without the COX-2 inhibitor. Such a dose of hydrocodone is preferably from about 5 to about 2000 mg, and preferably at least about 15 mg hydrocodone.

The invention further relates to a method of effectively treating pain in humans, comprising administering to a human patient a therapeutically effective amount of a COX-2 inhibitor together with a dose of an opioid analgesic, such that the combination provides an analgesic effect which is at least about 5 (and preferably at least about 10) times greater than that obtained with the dose of opioid analgesic alone. In certain embodiments, the synergistic combination provides an analgesic effect which is up to about 30–40 times greater than that obtained with the dose of opioid analgesic alone. In certain preferred embodiments, the doses of the COX-2 inhibitor and the opioid analgesic are administered orally. In further preferred embodiments, the doses of the COX-2 inhibitor and the opioid analgesic are administered in a single oral dosage form. In certain preferred embodiments, the dose of opioid analgesic would be sub-therapeutic if administered without the dose of COX-2 inhibitor. In other preferred embodiments, the dose of opioid analgesic is effective to provide analgesia alone, but the dose of opioid provides at least a five-fold greater analgesic effect than typically obtained with that dose of opioid alone.

The invention further relates to the use of a pharmaceutical combination of a COX-2 inhibitor together with an opioid analgesic to provide effective pain management in humans.

The invention further relates to the use of a COX-2 inhibitor in the manufacture of a pharmaceutical preparation containing a COX-2 inhibitor and an opioid analgesic for the treatment of pain.

The invention further relates to the use of an opioid analgesic in the manufacture of a pharmaceutical preparation containing a COX-2 inhibitor and an opioid analgesic for the treatment of pain.

The invention is also directed to a method for providing effective pain management in humans, comprising administering an analgesically effective or sub-therapeutic amount of an opioid analgesic; and administering an effective amount of a COX-2 inhibitor in an amount effective to augment the analgesic effect provided by said opioid analgesic. The COX-2 inhibitor can be administered before, simultaneously with, or after administration of the opioid analgesic, as long as the dosing interval of the COX-2 inhibitor overlaps with the dosing interval of the opioid analgesic (or its analgesic effects). In other words, according to the method of the present invention, in certain preferred embodiments the COX-2 inhibitor need not be administered in the same dosage form or even by the same route of administration as the opioid analgesic. Rather, the method is directed to the surprising synergistic and/or additive benefits obtained in humans, when analgesically effective levels of an opioid analgesic have been administered to a human, and, prior to or during the dosage interval for the opioid analgesic or while the human is experiencing analgesia, an effective amount of COX-2 inhibitor to augment the analgesic effect of the opioid analgesic is administered. If the COX-2 is administered prior to the administration of the opioid analgesic, it is preferred that the dosage intervals for the two drugs overlap, i.e., such that the analgesic effect over at least a portion of the dosage interval of the opioid analgesic is at least partly attributable to the COX-2 inhibitor.

In an additional method of the invention, the surprising synergistic and/or additive benefits obtained in humans are achieved when analgesically effective levels of a COX-2 inhibitor have been administered to a human, and, during the dosage interval for the COX-2 inhibitor or while the human is experiencing analgesia by virtue of the administration of a COX-2 inhibitor, an effective amount of an opioid analgesic to augment the analgesic effect of the COX-2 inhibitor is administered.

In a further embodiment of the present invention, the invention comprises an oral solid dosage form comprising an analgesically effective amount of an opioid analgesic together with an amount of a COX-2 inhibitor or pharmaceutically acceptable salt thereof which augments the effect of the opioid analgesic.

Optionally, the oral solid dosage form includes a sustained release carrier which causes the sustained release of the opioid analgesic, or both the opioid analgesic and the COX-2 inhibitor when the dosage form contacts gastrointestinal fluid. The sustained release dosage form may comprise a plurality of substrates which include the drugs. The substrates may comprise matrix spheroids or may comprise inert pharmaceutically acceptable beads which are coated with the drugs. The coated beads are then preferably overcoated with a sustained release coating comprising the sustained release carrier. The matrix spheroid may include the sustained release carrier in the matrix itself; or the matrix may comprise a normal release matrix containing the drugs, the matrix having a coating applied thereon which comprises the sustained release carrier. In yet other embodiments, the oral solid dosage form comprises a tablet core containing the drugs within a normal release matrix, with the tablet core being coated with a sustained release coating comprising the sustained release carrier. In yet further embodiments, the tablet contains the drugs within a sustained release matrix comprising the sustained release carrier. In yet further embodiments, the tablet contains the opioid analgesic within a sustained release matrix and the COX-2 inhibitor coated into the tablet as an immediate release layer.

In many preferred embodiments of the invention, the pharmaceutical compositions containing the COX-2 inhibitors and opioid drugs set forth herein are administered orally. Such oral dosage forms may contain one or both of the drugs in immediate or sustained release form. For ease of administration, it is preferred that the oral dosage form contains both drugs. The oral dosage forms may be in the form of tablets, troches, lozenges, aqueous or oily suspensions, dispersible powders or granules, emulsions, multiparticulate formulations, syrups, elixirs, and the like.

The pharmaceutical compositions containing the COX-2 and/or the opioid drugs set forth herein may alternatively be in the form of microparticles (e.g., microcapsules, microspheres and the like), which may be injected or implanted into a human patient, or other implantable dosage forms known to those skilled in the art of pharmaceutical formulation. For ease of administration, it is preferred that such dosage forms contain both drugs.

Additional pharmaceutical compositions comtemplated by the invention further include transdermal dosage forms, suppositories, inhalation powders or sprays, and buccal tablets.

The combination of COX-2 inhibitor and opioid analgesic may further be administered by different routes of administration.

It should be understood that for purposes of the present invention, the following terms have the following meanings:

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain experienced versus side effects) to analgesic treatment by a physician as well as subjective evaluation of therapeutic treatment by the patient undergoing such treatment. The skilled artisan will understand that effective analgesia will vary according to many factors, including individual patient variations.

The term "opioid analgesic" is defined for purposes of the present invention as the drug in its base form, or a pharmaceutically acceptable salt or complex thereof.

The term "COX-2 inhibitor" is defined for purposes of the present invention as the drug in its base form, or a pharmaceutically acceptable salt or complex thereof.

The term "sustained release" is defined for purposes of the present invention as the release of the drug (opioid analgesic) from the transdermal formulation at such a rate that blood (e.g., plasma) concentrations (levels) are maintained within the therapeutic range (above the minimum effective analgesic concentration or "MEAC") but below toxic levels over a period of time of about 12 hours or longer.

The term "steady state" means that the blood plasma concentration curve for a given drug has been substantially repeated from dose to dose.

The term "minimum effective analgesic concentration" is defined for purposes of this invention as the minimum effective therapeutic blood plasma level of the drug at which at least some pain relief is achieved in a given patient. It will be well understood by those skilled in the medical art that pain measurement is highly subjective and great individual variations may occur among patients.

DETAILED DESCRIPTION

Figure 1:
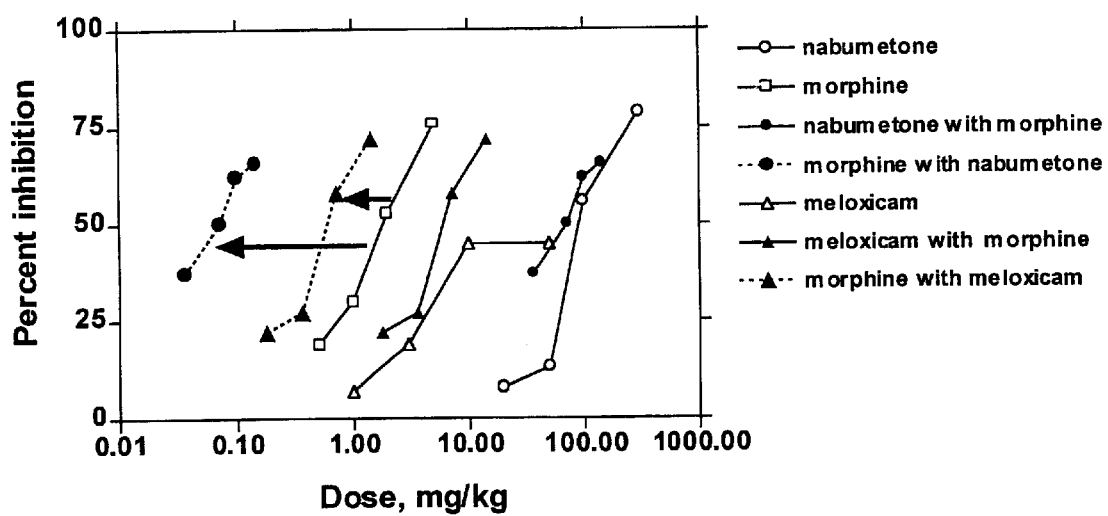
FIG. 1 describes the percent inhibition (ED50) plotted against the dose (mg/kg) for nabumetone, meloxicam, and morphine alone, and for combinations of nabumetone=morphine, and meloxicam=morphine.

The COX-2 inhibitors which are useful in the present invention will have similar anti-inflammatory, antipyretic and analgesic properties as compared to conventional non-steroidal anti-inflammatory drugs and in addition will inhibit hormone-induced uterine contractions and have potential anti-cancer effects, but will have a diminished ability to induce some of the mechanism-based side effects. In particular, such COX-2 inhibitors should have a reduced potential for gastrointestinal toxicity, a reduced potential for renal side effects, a reduced effect on bleeding times and a lessened ability to induce asthma attacks in aspirin-sensitive asthmatic subjects. COX-2 inhibitors have been reported in the art and many chemical structures are known to produce inhibition of cyclooxygenase-2. For purposes of the present invention, the term "COX-2 inhibitor" is defined as all compounds which would possess COX-2 inhibitory activity and which preferably have at least 9-fold greater specificity for COX-2 over COX-1, either in-vitro (as determined, e.g., by IC50 measurements) or in-vivo (as determined, e.g., by ED50 measurements). Such COX-2 inhibitors will be useful in conjunction with the present invention and are considered to be encompassed by the appended claims. Preferably, the COX-2 inhibitors used in the present invention demonstrate an in-vitro IC50 and/or in-vivo ED50 ratio for COX-1 to COX-2 of approximately 20-fold or greater, more preferably 100-fold or greater, or most preferably in certain embodiments 1000-fold or greater.

Certain preferred COX-2 inhibitors include celecoxib (SC-58635), DUP-697, flosulide (CGP-28238), meloxicam, 6-methoxy-2 naphthylacetic acid (6-MNA), Vioxx (rofecoxib) (MK-966), nabumetone (prodrug for 6-MNA), nimesulide, NS-398, SC-5766, SC-58215, T-614; or combinations thereof.

There are a number of COX-2 inhibitors in development as of mid-1998. These include meloxicam (commercially available in the U.K. as of 1996 from Boerhinger-Ingelheim); nimesulide (launched in 1985 in Europe from Hesinn); nabumetone (6-MNA is active metabolite) (commercially available as Relafin™ in the U.S.); celecoxib (SC-58635) (NDA filing by Searle estimated in Sep. 1998); Vioxx (MK-966, L745337) (NDA filing by Merck estimated in November 1998); D-1367 (Chiroscience; in Phase I in the U.K.); T-614 (Toyama; in Phase II in Japan and Phase I in the U.K.); and SC-57666 (Monsanto; in Phase I in the U.S.).

In trials discussed at the 1996 annual meeting of the American College of Rheumatology, celecoxib was demonstrated to be efficacious in patients and devoid of gastrointestinal side effects in normal volunteers (Scrip 2175, Oct. 25, 1996, p. 15). In studies in normal volunteers, 128 subjects received celecoxib, 100 mg or 200 mg twice a day, or naproxen, or placebo, for one week. In the celecoxib groups and subjects who received placebo, there were no gastrointestinal signs or symptoms, whereas in the naproxen group, 20% of subjects experienced gastrointestinal signs and symptoms. Further, in normal volunteers, celecoxib caused no alterations in platelet function. In a study in patients, 293 patients, with osteoarthritis received celecoxib, 40 mg, 100 mg, or 200 mg, or placebo twice a day for two weeks. Celecoxib reduced symptoms significantly, and drop-out rates in the higher dose celcoxib groups were lower than for placebo. Patients with rheumatoid arthritis received celecoxib 100 mg, 200 mg, or 400 mg, or placebo,twice a day for four weeks. As in patients with osteoarthritis, symptom scores were improved in patients receiving celecoxib compared to placebo, and drop-out rates were lower in patients taking celecoxib. COX-2 inhibitors have been reported in the art and many chemical structures are known to produce inhibition of cyclooxygenase-2.

COX-2 inhibitors are described in U.S. Pat. Nos. 5,616,601; 5,604,260; 5,593,994; 5,550,142; 5,536,752; 5,521,213; 5,639,780; 5,604,253; 5,552,422; 5,510,368; 5,436,265; 5,409,944; and 5,130,311, all of which are incorporated by reference. Many COX-2 inhibitors may be described chemically as aryl sulfonamides. Indeed, both celecoxib and Vioxx, which are considered to be "super-selective", are aryl sulfonamides, and more specifically, benzenesulfonamides. These compounds will be useful in the methods and compositions of the present invention. However, one skilled in the art will appreciate that many additional COX-2 inhibitors have been identified in the art and would be useful in conjunction with the methods and compositions of the present invention.

The use of structure-activity relationships in evaluating COX inhibitors is problematic because these COX inhibitors are suicide enzymes. Thus, when analyzed in an in-vitro assay, the IC50 value will change over time. For this reason, published IC50's for common COX inhibitors have been reported as values varying by more than two orders of magnitude from laboratory to laboratory. This makes it difficult to compare the value for COX-1 inhibition obtained from one laboratory to the value for COX-2 inhibition obtained from another laboratory. (See, for example D. E. Griswold and J. L. Adams, Med. Res. Rev. 16: 181–206). Thus, it is preferable that when studying COX inhibitors to compare their relative potencies, comparisons only be made using results from the same assay, conducted at the same time. When using previously generated data it is preferable to take data only from lists of several compounds that have been generated by one group so that the relative potencies may be determined. Table 1 below provides representative data for representative NSAIDs and certain COX-2 inhibitor compounds. The data have been collected from a number of different sources, and were chosen from available laboratories, using references which report on several compounds in the same paper, and which contain data that are relatively compatible to data obtained from certain other laboratories (i.e., within a reasonable range of variation, with the understanding that results from different laboraties can vary up to three orders of magnitude for agents that act as suicide enzymes). It should be kept in mind that most of the values reported in Table 1 are from in-vitro assays (except where potency is reported as mg/kg). The literature confirms that ratios of COX-1/COX-2 potency are generally kept in-vivo, but this is not always true. For example, indomethacin is always COX-1-selective in-vitro and in-vivo, but naproxen, which is COX-1-selective in-vitro, is often (but not always) COX-2-selective in-vivo. In part, this is due to the highly artificial in-vitro assay conditions used. The first two structural series were recognized as COX inhibitors that exhibited remarkably little ulcerogenic activity. These early compounds included the aryl sulfonamides nimesulide, NS-398, and CGP 23238 and the 1,2-diarylheterocycles Dup-697 and SC-58125. Griswold and Adams describe structure activity relationships in some detail (Med. Res. Rev. 16: 282–206, 1996).

TABLE 1

Selectivity of selected cyclooxygenase inhibitors for COX-1 and Cox-2

| Drug | COX-1 IC50, $\mu$M | COX-2 IC50, $\mu$M | COX-1/COX-2 | Ref |
|---|---|---|---|---|
| Aspirin | 1.67 | 278 | 0.004 | l |
| | 32.4 mg/kg | 198 mg/kg | 0.16 | m |
| Salicylate | 254 | 725 | 0.36 | l |
| Ibuprofen | 4.85 | 72.8 | 0.067 | l |
| | 9.2 | 18.3 | 0.5 | n |
| Naproxen | 4.8 | 28.4 | 0.17 | a |
| | 0.6 | 2.0 | 0.3 | b |
| | 6.6 | 3.9 | 1.7 | c |
| | 15.6 | 28 | 0.56 | n |
| Diclofenac | 0.04 | 0.1 | 0.4 | d |
| | 2.7 | 20.5 | 0.13 | a |
| | 1.5 | 1.05 | 1.4 | c |
| | 0.018 | 0.012 | 1.5 | e |
| Indomethacin | 0.1 | 0.9 | 0.11 | d |
| | 13.5 | >1000 | <0.013 | a |
| | 0.0015 | 0.0089 | 0.15 | e |
| | 2.35 mg/kg | 0.67 mg/kg | 3.3 | m |
| S-ketoprofen | 0.11 | 0.18 | 0.61 | n |
| Tenidap | 0.39 | 47.8 | 0.008 | f |
| Piroxicam | 17.7 | >500 | <0.035 | a |
| | 1.07 mg/kg | 0.76 mg/kg | 1.4 | m |
| Meloxicam | 3.27 | 0.25 | 13 | k |
| | 2.47 mg/kg | 0.12 mg/kg | 20 | m |
| Nimesulide | 70 | 1.27 | 55 | b |
| | 9.2 | 0.52 | 17.7 | n |
| NS-398 | >100 | 0.1 | >1000 | g |
| | 75 | 1.77 | 42 | b |
| | 16.8 | 0.1 | 168 | N |
| 6-MNA | 64 | 94 | 0.7 | A |
| | 240 | 35 | 7 | H |
| | 278 | 187 | 1.5 | I |
| CGP 28238 (flosulide) | 72.3 | 0.015 | 5000 | E |
| SC-58125 | >100 | 0.09 | >1100 | j |
| | 38.7 | 0.27 | 143 | |
| Celecoxib (SC-58635) | 15 | 0.04 | 375 | o |
| Vioxx (l 745,337) | 369 | 1.5 | 246 | n |
| Dup-697 | 0.8 | 0.01 | 80 | d |

[a] O. Laneuville et al, J. Pharmacol. Exp. Ther. 271: 927, 1994
[b] J. Barnett et al Biochim. Biophys. Acta 1209: 130, 1994
[c] J. R. Vane and R. M. Botting. Inflamm. Res. 44: 1, 1995
[d] J. K. Gierse et al, Biochem. J. 305: 479, 1995
[e] T. Klein et al, Biochem. Pharmacol. 48: 1605, 1994
[f] B. Battistini et al, Drug News Perspect. 7: 501, 1994
[g] R. A. Copeland et al, Proc. Natl. Acad, Sci. USA 91: 11202, 1994
[h] E. A. Mead et al, J. Biol. Chem. 268: 6610, 1993
[i] P. Patrignani et al, J. Pharmacol. Exp. Ther. 271: 1705, 1994
[j] P. Isakson, et al, Adv. Prost. Throm. Res. 23: 49, 1995
[k] M. Pairet, et al Inflamm. Res. 47: 270–276, 1998
[l] J. A. Mitchell et al Proc. Natl. Acad. Sci. USA 90: 11693–11697, 1994
[m] G. Engelhardt et al Inflamm. Res. 44: 423433, 1995
[n] P. Patrignani et al J Phys Pharmacol. 48: 623–631, 1997
[o] T D Penning et al J Med Chem 40: 1347–1365, 1997

For example, as reported by Famaey J P, *Inflamm Res* November 1997; 46(11):437–446, nimesulide, a sulfonanilide compound with anti-inflammatory properties, possessed a pharmacological profile suggesting that it might be a selective inhibitor of COX-2. In several in vitro assays using either purified COX-2 and COX-1 preparations or cell preparations (both from animal and human origins) expressing COX-1 or COX-2, ten out of eleven different groups demonstrated that nimesulide selectively inhibits COX-2. The COX-2/COX-1 inhibitory ratio was reported to vary, according to the assay preparation, from about 0.76 to 0.0004 i.e. a 1.3 to 2,512-fold higher selectivity for COX-2 than for COX-1. Further, an in-vivo whole blood assay performed on healthy volunteers demonstrated a significant fall in COX-2 PGE2 production without any effect on COX-1 TXB2 production (subjects treated with nimesulide 00 mg b.i.d. for 2 weeks) versus no effect on COX-2 PGE2 and an almost total suppression of COX-1 TXB2 in subjects treated with aspirin (300 mg t.i.d. for 2 weeks). Nimesulide can thus be considered a relatively selective COX-2 inhibitor. At the recommended dosage of 100 mg b.i.d., it is as effective an analgesic and anti-inflammatory agent as classical NSAIDs, and a well-tolerated drug with few side-effects according to large-scale open studies and a global evaluation of a large number of controlled and non-controlled comparative trials.

A non-limiting list of opioid analgesic drugs which may be utilized in the present invention include alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, salts thereof, complexes thereof; mixtures of any of the foregoing, mixed mu-agonists/antagonists, mu-antagonist combinations salts or complexes thereof, and the like. In certain preferred embodiments, the opioid analgesic is a mu or kappa opioid agonist. In additional preferred embodiments, the opioid analgesic is a selective kappa agonist.

In certain preferred embodiments, the opioid analgesic is selected from codeine, hydromorphone, hydrocodone, oxycodone, dihydrocodeine, dihydromorphine, diamorphine, morphine, tramadol, oxymorphone salts thereof, or mixtures thereof.

The present invention provides for analgesic preparations for oral administration that provide a combination of a COX-2 inhibitor or a pharmaceutically acceptable salt thereof and an opioid analgesic or a pharmaceutically acceptable salt thereof. The combination preferably provides a synergistic or at least additive effect for analgesic dosages.

Dosage levels of COX-2 inhibitor on the order of from about 0.005 mg to about 140 mg per kilogram of body weight per day are therapeutically effective in combination with an opioid analgesic. Alternatively, about 0.25 mg to about 7 g per patient per day of a COX-2 inhibitor is administered in combination with an opioid analgesic. For example, inflammation may be effectively treated by the administration of from about 0.005 to 50 mg of the COX-2 inhibitor per kilogram of body weight per day, or alternatively about 0.25 mg to about 3.5 g per patient per day.

The amount of COX-2 inhibitor that may be combined with the carrier materials to produce a single dosage form having COX-2 inhibitor and opioid analgesic in combination will vary depending upon the patient and the particular mode of administration. For example, a formulation intended for the oral administration of humans may contain from 0.25 mg to 5 g of COX-2 inhibitor compounded with an appropriate and convenient amount of carrier material which may vary from about 5 to about 95 percent of the total composition. Unit dosages will generally contain between from about 0.5 mg to about 1500 mg of a COX-2 inhibitor, and typically 25 mg, 50 mg, 100 mg, 200 mg, 300 mg, 400 mg, 500 mg, 600 mg, 800 mg, or 1000 mg, etc., up to 1500 mg.

In one embodiment, the COX-2 inhibitor is provided in a sustained release oral dosage form with hydromorphone as the therapeutically active opioid in an amount from about 2 mg to about 64 mg hydromorphone hydrochloride. Alternatively, the dosage form may contain molar equivalent amounts of other hydromorphone salts or of the hydromorphone base. In another embodiment, the opioid analgesic comprises morphine, and the sustained release oral dosage forms of the present invention include from about 2.5 mg to about 800 mg morphine, by weight. In yet another embodiment, the opioid analgesic comprises oxycodone and the sustained release oral dosage forms include from about 2.5 mg to about 800 mg oxycodone. The opioid analgesic may comprise hydrocodone, and the sustained release oral dosage forms may include analgesic doses from about 8 mg to about 50 mg of hydrocodone per dosage unit. The opioid analgesic may comprise tramadol and the sustained release oral dosage forms may include from about 25 mg to 800 mg tramadol per dosage unit. The dosage form may contain more than one opioid analgesic to provide a substantially equivalent therapeutic effect.

Preferred combinations of the invention comprise an effective amount of a COX-2 inhibitor selected from the group consisting of nimesulide, melorican, and flosulide, and an effective amount of an opioid analgesic selected from the group consisting of tramadol, hydromorphone, morphine, oxycodone, hydrocodone and dihydrocodeine in the ratios set forth in Table I. In certain preferred embodiments, the ratio of the afore-mentioned opioids to the afore-mentioned COX-2 inhibitors is set forth in Table 1.

TABLE I

Ratios of Opiates to COX-2 Inhibitors

COX-2 INHIBITORS

| OPIATES | CELECOXIB | FLOSULIDE | MELOXICAM | NABUMETONE | NIMESULIDE | T614 | MK966 |
| --- | --- | --- | --- | --- | --- | --- | --- |
| MORPHINE | 0.001–1 | 0.001–1 | 0.05–50 | 0.0005–1 | 0.001–5 | 0.001–1 | 0.001–10 |
| METHADONE | 0.0001–1 | 0.0001–1 | 0.01–10 | 0.0001–1 | 0.001–1 | 0.0001–1 | 0.001–1 |
| MEPERIDINE | 0.01–100 | 0.001–1 | 0.001–50 | 0.004–1 | 0.01–1 | 0.01–1 | 1–100 |
| LEVORPHANOL | 0.004–1 | 0.0001–1 | 0.001–1 | 0.00001–0.01 | 0.0002–1 | 0.0001–1 | 0.0001–1 |
| HYDROMORPHONE | 0.0003–3 | 0.0001–1 | 0.00001–1 | 0.0001–0.1 | 0.0001–1 | 0.0001–1 | 0.0001–1 |
| OXYCODONE | 0.001–10 | 0.0001–1 | 0.0001–1 | 0.0001–1 | 0.0001–1 | 0.0001–1 | 0.0001–1 |
| HYDROCODONE | 0.001–10 | 0.0001–1 | 0.00011 | 0.0001–1 | 0.0001–1 | 0.0001–1 | 0.0001–1 |
| CODEINE | 0.005–50 | 0.001–4 | 0.001–20 | 0.001–1 | 0.001–10 | 0.001–1 | 0.001–10 |

In other words, Table I describes test of ratios of morphine:celecoxib from about 0.001:1 to about 1:1; for methadone to flosulide the ratio is from about 0.0001:1 to about 1:1, and so on.

In certain preferred embodiments according to the present invention, an oral dosage form is preferred which includes the following opioid/COX-2 inhibitor combinations: Morphine 40 mg plus 40 mg flosulide; morphine 40 mg plus 6 mg nimesulide; oxycondone 20 mg plus 20 mg flosulide; oxycodone 40 mg plus 4 mg nimesulide; hydromorphone 5 mg plus 20 mg flosulide; or hydromorphone 5 mg plus 4 mg nimesulide.

The dosage administered will, of course, vary depending upon known factors such as the pharmacodynamic characteristics of each agent of the combination and its mode and route of administration and upon the age, health and weight of the patient. The dosage will also depend upon the nature and extent of symptoms, concurrent treatment, if any, frequency of treatment and the desired result. A composition comprising any of the above-identified combinations of opioid analgesics and COX-2 inhibitors may be administered in divided doses ranging from 2 to 6 times per day or in a sustained release form that will provide a rate of release effective to attain the desired results.

The optimal COX-2 inhibitor and opioid analgesic ratios are determined by standard assays well known in the art for determining opioid and analgesic activity. For example, the phenyl-p-benzoquinone test may be used to establish analgesic effectiveness. The phenyl-p-benzoquinone induced writhing test in mice (H. Blumberg et al., 1965, *Proc. Soc. Exp. Med.* 118:763–766) hereby incorporated by reference; and known modifications thereof) is a standard procedure which may be used for detecting and comparing the analgesic activity of different classes of analgesic drugs with a good correlation with human analgesic activity. Data for the mouse, as presented in an isobologram, can be translated to other species where the orally effective analgesic dose of the individual compounds are known or can be estimated. The method consists of reading the percent ED50 dose for each dose ratio on the best fit regression analysis curve from the mouse isobologram, multiplying each component by its effective species dose, and then forming the ratio of the amount of COX-2 inhibitor and opioid analgesic. This basic correlation for analgesic properties enables estimation of the range of human effectiveness (E. W. Pelikan, 1959, *The Pharmacologist* 1:73; hereby incorporated by reference).

Application of an equieffective dose substitution model and a curvilinear regression analysis utilizing all the data for the individual compounds and various dose ratios for the combinations establishes the existence of unexpectedly enhanced analgesic activity of combinations of COX-2 inhibitor and opioid analgesic, i.e., the resulting activity is greater than the activity expected from the sum of the activities of the individual components.

The present invention encompasses immediate release dosage forms of an effective analgesic amount of a COX-2 inhibitor and opioid analgesic combination. An immediate release dosage form may be formulated as a tablet or multiparticulate which may be encapsulated. Other immediate release dosage forms known in the art can be employed.

Compositions of the invention present the opportunity for obtaining relief from moderate to severe pain with or without inflammation. Due to the synergistic and/or additive effects provided by the inventive combination of opioid analgesic and COX-2 inhibitor, it may be possible to use reduced dosages of each of COX-2 inhibitor and opioid analgesic. By using lesser amounts of other or both drugs, the side effects associated with each may be reduced in number and degree. Moreover, the inventive combination avoids side effects to which some patients are particularly sensitive.

The present invention encompasses a method of inhibiting COX-2 and treating COX-2 mediated diseases comprising administering to a patient in need of such treatment a non-toxic therapeutically effective amount of the COX-2 inhibitor and opioid analgesic combination of the present invention. These diseases include moderate to severe pain arising from many different etiologies, including but not limited to cancer pain and post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and injuries. Further, the combination of COX-2 inhibitor and opioid analgesic is useful as an alternative to conventional non-steroidal anti-inflammatory drugs or combinations of NSAID'S with other drugs particularly where such non-steroidal anti-inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

The sustained release dosage forms of the present invention generally achieve and maintain therapeutic levels substantially without significant increases in the intensity and/or degree of concurrent side effects, such as nausea, vomiting or drowsiness, which are often associated with high blood levels of opioid analgesics. There is also evidence to suggest that the use of the present dosage forms leads to a reduced risk of drug addiction.

The combination of COX-2 inhibitor and oral opioid analgesics may be formulated to provide for an increased duration of analgesic action allowing once-daily dosing. These formulations, at comparable daily dosages of conventional immediate release drug, are associated with a lower incidence in severity of adverse drug reactions and can also be administered at a lower daily dose than conventional oral medication while maintaining pain control.

The combination of COX-2 inhibitor and an opioid analgesic can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. Ampoules are convenient unit dosages. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combination of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

The method of treatment and pharmaceutical formulations of the present invention may further include one or more drugs in addition to a COX-2 inhibitor and an opioid analgesic, which additional drug(s) may or may not act synergistically therewith. Examples of such additional drugs include non-steroidal anti-inflammatory agents, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, and the like. Other suitable additional drugs which may be included in the dosage forms of the present invention include acetaminophen, aspirin, and other non-opioid analgesics.

Controlled Release Dosage Forms

The COX-2 inhibitor and opioid analgesic combination can be formulated as a controlled or sustained release oral formulation in any suitable tablet, coated tablet or multiparticulate formulation known to those skilled in the art. The sustained release dosage form may optionally include a sustained released carrier which is incorporated into a matrix along with the opioid, or which is applied as a sustained release coating.

The sustained release dosage form may include the opioid analgesic in sustained release form and COX-2 inhibitor in sustained release form or in immediate release form. The COX-2 inhibitor may be incorporated into the sustained release matrix along with the opioid; incorporated into the sustained release coating; incorporated as a separated sustained release layer or immediate release layer; or may be incorporated as a powder, granulation, etc., in a gelatin capsule with the substrates of the present invention. Alternatively, the sustained release dosage form may have the COX-2 inhibitor in sustained release form and the opioid analgesic in sustained release form or immediate release form.

An oral dosage form according to the invention may be provided as, for example, granules, spheroids, beads, pellets (hereinafter collectively referred to as "multiparticulates") and/or particles. An amount of the multiparticulates which is effective to provide the desired dose of opioid over time may be placed in a capsule or may be incorporated in any other suitable oral solid form.

In one preferred embodiment of the present invention, the sustained release dosage form comprises such particles containing or comprising the active ingredient, wherein the particles have diameter from about 0.1 mm to about 2.5 mm, preferably from about 0.5 mm to about 2 mm.

In certain embodiments, the particles comprise normal release matrixes containing the opioid analgesic with or without the COX-2 inhibitor. These particles are then coated with the sustained release carrier in embodiments where the COX-2 inhibitor is immediately released, the COX-2 inhibitor may be included in separate normal release matrix particles, or may be co-administered in a different immediate release composition which is either enveloped within a gelatin capsule or is administered separately. In other embodiments, the particles comprise inert beads which are coated with the opioid analgesic with or without the COX-2 inhibitor. Thereafter, a coating comprising the sustained release carrier is applied onto the beads as an overcoat.

The particles are preferably film coated with a material that permits release of the opioid (or salt) and if desired, the COX-2 inhibitor, at a sustained rate in an aqueous medium. The film coat is chosen so as to achieve, in combination with the other stated properties, a desired in-vitro release rate. The sustained release coating formulations of the present invention should be capable of producing a strong, continuous film that is smooth and elegant, capable of supporting pigments and other coating additives, non-toxic, inert, and tack-free.

Coatings

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the opioid in desired areas of the gastrointestinal (GI) tract, e.g., the stomach or small intestine, such that an absorption profile is provided which is capable of providing at least about twelve hour and preferably up to twenty-four hour analgesia to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the opioid analgesic (with or without the COX-2 inhibitor) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described, e.g., in detail in U.S. Pat. Nos. 5,273,760 and 5,286,493, assigned to the Assignee of the present invention and hereby incorporated by reference.

Other examples of sustained release formulations and coatings which may be used in accordance with the present invention include Assignee's U.S. Pat. Nos. 5,324,351; 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Röhm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When the aqueous dispersion of hydrophobic material is used to coat inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the opioid to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Preformulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as poreformers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos.

3,845,770; 3,916,889; 4,063,064; and 4,088,864 (all of which are hereby incorporated by reference). The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in-vitro dissolution rates of the opioid within the preferred ranges and that releases the opioid in a pH-dependent or pH-independent manner. The materials suitable for inclusion in a controlled release matrix will depend on the method used to form the matrix.

For example, a matrix in addition to the opioid analgesic and (optionally) COX-2 may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts (or softens to the extent necessary to be extruded) may be used in accordance with the present invention.

Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit® RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25 and 90 C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30 to about 200 C., preferably from about 45 to about 90 C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100 C.

Suitable hydrophobic materials which may be used in accordance with the present invention include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25 and 90 C. are preferred. Of the long chain hydrocarbon materials, fatty (aliphatic) alcohols are preferred in certain embodiments. The oral dosage form may contain up to 60% (by weight) of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a controlled release matrix may also contain suitable quantities of other materials, e.g. diluents, lubricants, binders, granulating aids, colorants, flavorants and glidants that are conventional in the pharmaceutical art.

Processes for Preparing Matrix—Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opioid or an opioid salt; (b) mixing the hydroxyalkyl cellulose containing granules with at least one $C_{12}$–$C_{36}$ aliphatic alcohol; and (c) optionally, compressing and shaping the granules. Preferably, the granules are formed by wet granulating the hydroxyalkyl cellulose/opioid with water. In a particularly preferred embodiment of this process, the amount of water added during tie wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598, assigned to the Assignee of the present invention and hereby incorporated by reference in its entirety.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the *Handbook of Pharmaceutical Excipients*, American Pharmaceutical Association (1986), incorporated by reference herein.

Melt Extrusion Multiparticulates

The preparation of a suitable melt-extruded matrix according to the present invention may, for example, include the steps of blending the opioid analgesic, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553–1593 (1980), incorporated by reference herein.

In yet another preferred embodiment, the extrudate can be shaped into tablets as set forth in U.S. Pat. No. 4,957,681 (Klimesch, et. al.), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opioid analgesic compound utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the therapeutically active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

DETAILED DESCRIPTION OF PREFERRED EMBODIMENTS

The following examples illustrate various aspects of the present invention. They are not to be construed to limit the claims in any manner whatsoever.

EXAMPLES 1–2

Evaluation of Combination of Morphine and Nabumetone (Example 1) and Morphine and Meloxicam (Example 2)

In Examples 1–2, COX-2 inhibitor-opiate synergy were examined by examining nabumetone (Example 1) and meloxicam (Example 2) in a Phenylquinone (PPQ) stretching (writhing) test.

Nabumetone is not intrinsically COX-2-selective, but is evaluated here because its use is associated with extremely low ulcerogenesis. Nabumetone is a prodrug, giving rise to the actual COX-2 inhibitor, 6-methoxy-2-naphthylacetic acid (6-MNA). (see Table 1). The low ulcerogenic potential of nabumetone may be due to the pH-dependent formation of 6-MNA. This does not occur at low pH values, such as those found in the gastric mucosa. Thus, COX-2 selectivity appears to be functional. In clinical trials, nabumetone has been found to be quite efficacious, with extremely little ulcerogenesis. In a trial in patients with osteoarthritis, nabumetone was compared to diclofenac. It was found to be as efficacious as diclofenac (it is extremely impotent, requiring 1500 mg daily), however, none of the 382 patients treated with nabumetone experienced gastrointestinal toxicity (S. H. Roth et al, J. Rheumatol. 21: 1118, 1994). In a report of 1-year follow-up of patients treated with nabumetone, the incidence of ulcers was only 0.5% (PDR 1995, p. 2396).
Methods Isobolographic analysis of drug interaction was performed in male ICR mice. At time=0, meloxicam or nabumetone or vehicle was administered p.o. At time (T)=9 minutes, morphine or vehicle was administered p.o. At T=29 minutes, PPQ (phenyl-p-benzylquinone), 2 mg/kg, was injected i.p. At T=36 minutes, the number of abdominal stretches was counted for each mouse for 1 minute. At T=40 minutes, stretches were again counted for 1 minute. There were 6–8 mice per dose.

The concentrations of morphine used for its dose-response were 0.5, 1, 2, and 5 mg/kg. The concentrations of nabumetone used for its dose-response were 20, 50, 100, and 300 mg/kg. The concentrations of meloxicam used for its dose-response were 1, 3, 10, and 50 mg/kg.

The % inhibition of PPQ stretching (writhing) test was calculated as follows:

=1−{[total # stretches at two countings with drug]/[total # stretches at two countings with vehicle]}×100

ED50 (the dose of drug that caused an inhibition of 50%) was determined by nonlinear regression. When combinations of morphine and meloxicam or nabumetone were administered, the ratio was always set at 1:10 or 1:1000, respectively. For the combination studies, the following were used: morphine/nabumetone were 0.036/36, 0.072/72, 0.1/100, and 0.144/144 mg/kg, morphine/meloxicam were 0.18/1.8, 0.36/3.6, 0.72/7.2, and 1.44/14.4 mg/kg. The ED50 for each drug in the combination was determined by simple calculation of the amount of each in the combination at the ED50 combination dose. The ED50 results for Example 1 (nabumetone) versus morphine are set forth below:

nabumetone:

morphine ED50=1.86 mg/kg po (confidence interval 1.39–2.5)

nabumetone ED50 92.1 mg/kg po (slight extrapolation)

with combination dose-response using morphine:nabumetone 1:1000

ED50 morphine=0.06 (confidence interval is 0.02 to 0.17)

ED50 nabumetone=64.5.

As can be seen from the ED50 results, nabumetone significantly increased the potency of morphine. While morphine did not affect the potency of nabumetone in a statistically significant manner, it did shift the ED50 results to an extent which suggests that increasing the ratio of nabumetone to morphine may result in two-way synergy. In view of this result, the combination of a much more potent COX-2 inhibitor such as celecoxib will provide statistically significant two-way synergy. In such a combination, the opioid will be seen to significantly potentiate the analgesic effecticacy of celecoxib.

The ED50 results for Example 2 (meloxicam) are set forth below:

meloxicam:

morphine ED50=1.86 mg/kg po meloxicam ED50 15.2 mg/kg po (slight extrapolation)

with combination dose-response using morphine:meloxicam 1:10

ED50 morphine=0.62

ED50 meloxicam=6.22.

As can be seen from the ED50 results, meloxicam significantly increased the potency of morphine, whereas morphine did not affect the potency of meloxicam. Morphine did however, allow meloxicam to reach better efficacy—72% vs 45% inhibition.

The data obtained from Examples 1–2 are further represented in FIG. 1, which is a graph depicting the percent inhibition (ED50) plotted against the dose (mg/kg). FIG. 1 includes plots of dose-response data for nabumetone, meloxicam and morphine alone, and for combinations of nabumetone+morphine and meloxicam+morphine. As can be seen from the results set forth in FIG. 1, morphine did not shift the dose-response for nabumetone or meloxicam. However, nabumetone and meloxicam both shifted the dose-response for morphine (indicated by the arrows).

The interaction of morphine and flusolide can be demonstrated via an isobologram. (See, e.g., S. Loewe, *Pharm. Rev.*, 9; 237 (1957)) regarding the preparation and basis of an isobologram; hereby incorporated by reference).

Figure 2:
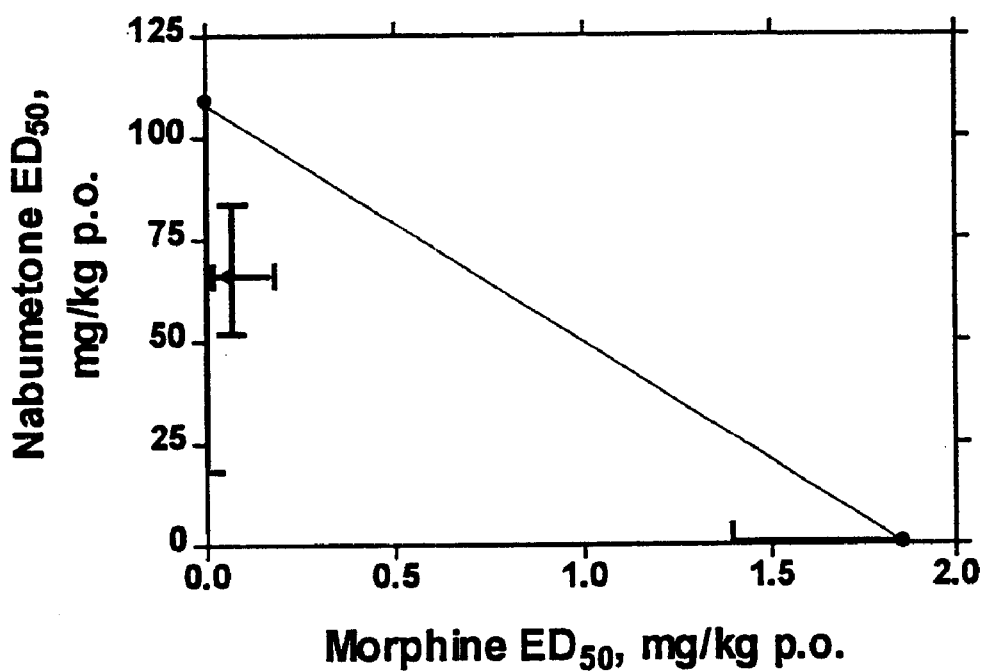
FIG. 2 is an isobologram for nabumetone in interaction with morphine.

FIG. 2 is an isobologram for nabumetone in interaction with morphine (included are 95% confidence intervals). The diagonal line joining the $ED_{50}$ values of the two drugs given separately represents the simple additivity of effects at different component ratios. $ED_{50}$ values falling under the curve (between the line and the origin) indicate superadditivity. As can be seen from FIG. 2, the combination of nabumetone and morphine exhibited synergism supporting the ratios of the combinations of these drugs set forth in Table II.

Figure 3:
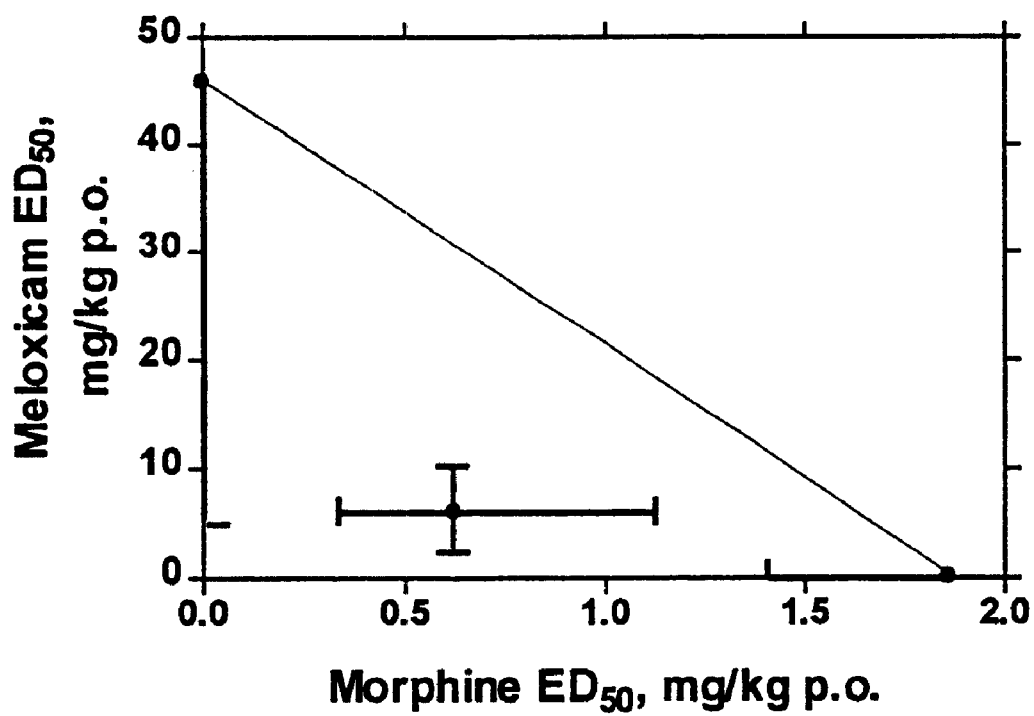
FIG. 3 is an isobologram for meloxicam in interaction with morphine.

FIG. 3 is an isobologram for meloxicam in interaction with morphine (included are 95% confidence intervals). As can be seen from FIG. 3, the combination of nabumetone and morphine exhibited synergism supporting the ratios of the combinations of these drugs set forth in Table II.

It is known to the art that data for the mouse, as presented in an isobologram, can be translated to other species where the orally effective analgesic dose of the individual compounds are known or can be estimated. Therefore, one of ordinary skill in the art will appreciate that this basic correlation for analgesic properties enables estimation of the range of human effectiveness.

CONCLUSION

While the invention has been described and illustrated with reference to certain preferred embodiments thereof, those skilled in the art will appreciate that obvious modifications can be made herein without departing from the spirit and scope of the invention. For example, effective dosages and the specific pharmacological responses may vary depending upon the ratios of the particular opioid to particular COX-2 inhibitor used, as well as the formulation and mode of administration. Such variations are contemplated to be within the scope of the appended claims.

What is claimed is:

1. A pharmaceutical composition comprising an analgesic combination consisting essentially of rofecoxib and/or at least one pharmaceutically acceptable salt thereof; and oxycodone and/or at least one pharmaceutically acceptable salt thereof.

2. The pharmaceutical composition according to claim 1, wherein the oxycodone and/or at least one pharmaceutically acceptable salt thereof would be sub-therapeutic administered without the rofecoxib and/or at least one pharmaceutically acceptable salt thereof.

3. The pharmaceutical composition according to claim 1, wherein the oxycodone and/or at least one pharmaceutically acceptable salt thereof; and rofecoxib and/or at least one pharmaceutically acceptable salt thereof are administered orally, via implant, parenterally, sublingually, rectally, topically, or via inhalation.

4. The pharmaceutical composition according to claim 1, which is selected from the group consisting of a tablet; a multiparticulate formulation for oral administration; a solution, a suspension or elixir for oral administration; an injectable formulation; an implantable device; a topical preparation; a suppository; a buccal tablet; or an inhalation formulation.

5. The pharmaceutical composition according to claim 1, which is a solid oral dosage form formulated as a tablet or capsule.

6. The pharmaceutical composition according to claim 1, wherein the ratio of oxycodone and/or at least one pharmaceutically acceptable salt thereof to rofecoxib and/or at least one pharmaceutically acceptable salt thereof is from about 0.0001:1 to about 1:1.

7. The pharmaceutical composition according to claim 1, wherein the rofecoxib and/or at least one pharmaceutically acceptable salt thereof synergistically potentiates the effect of the oxycodone and/or at least one pharmaceutically acceptable salt thereof but the oxycodone and/or at least one pharmaceutically acceptable salt thereof does not synergistically potentiate the effect of the rofecoxib and/or at least one pharmaceutically acceptable salt thereof.

8. The pharmaceutical composition according to claim 5, wherein the oral solid dosage form includes a sustained release carrier which causes the sustained release of the rofecoxib and/or at least one pharmaceutically acceptable salt thereof; the oxycodone and/or at least one pharmaceutically acceptable salt thereof; or both the oxycodone and/or at least one pharmaceutically acceptable salt thereof and the rofecoxib and/or at least one pharmaceutically acceptable salt thereof when the dosage form contacts gastrointestinal fluid.

9. The pharmaceutical composition according to claim 1, wherein the oxycodone and/or at least one pharmaceutically acceptable salt thereof is present in an amount from about 2.5 mg to about 800 mg.

10. The pharmaceutical composition according to claim 1, wherein the ratio of oxycodone and/or at least one pharmaceutically acceptable salt thereof to rofecoxib and/or at least one pharmaceutically acceptable salt thereof is from about 00001:1 to about 1:1.

11. A method of effectively treating pain in humans or other mammals, comprising administering to a patient an analgesic combination consisting essentially of rofecoxib and/or at least one pharmaceutically acceptable salt thereof; and oxycodone and/or at least one pharmaceutically acceptable salt thereof such that the dosing interval of the rofecoxib and/or at least one pharmaceutically acceptable salt thereof overlaps with the dosing interval of the oxycodone and/or at least one pharmaceutically acceptable salt thereof.

12. The method of claim 11, wherein the rofecoxib and/or at least one pharmaceutically acceptable salt thereof and the oxycodone and/or at least one pharmaceutically acceptable salt thereof are administered orally.

13. The method of claim 11, wherein the rofecoxib and/or at least one pharmaceutically acceptable salt thereof and the oxycodone and/or at least one pharmaceutically acceptable salt thereof are administered in a single oral dosage form.

14. The method of claim 11, wherein the oxycodone and/or at least one pharmaceutically acceptable salt thereof would be sub-therapeutic if administered without the rofecoxib and/or at least one pharmaceutically acceptable salt thereof.

15. The method of claim 11, wherein the rofecoxib and/or at least one pharmaceutically acceptable salt thereof is administered before, simultaneously with, or after administration of the oxycodone and/or at least one pharmaceutically acceptable salt thereof, such that the dosing interval of the rofecoxib and/or at least one pharmaceutically acceptable salt thereof overlaps with the dosing interval of the oxycodone and/or at least one pharmaceutically acceptable salt thereof.

16. The method of claim 11, wherein the oxycodone and/or at least one pharmaceutically acceptable salt thereof is present in an amount from about 2.5 mg to about 800 mg.

17. The method of claim 11, wherein the ratio of oxycodone and/or at least one pharmaceutically acceptable salt thereof to rofecoxib and/ar at least one pharmaceutically acceptable salt thereof is from about 0.0001:1 to about 1:1.

18. A method of reducing the oxycodone and/or at least one pharmaceutically acceptable salt thereof required to treat a patient affected with pain, comprising co-administering said oxycodone and/or at least one pharmaceutically acceptable salt thereof with rofecoxib and/or at least one pharmaceutically acceptable salt thereof, to augment the analgesia attributable to said oxycodone and/or at least one pharmaceutically acceptable salt thereof during at least a portion of the dosage interval of said oxycodone and/or at least one pharmaceutically acceptable salt thereof.

19. A method of reducing the amount of rofecoxib and/or at least one pharmaceutically acceptable salt thereof required to treat a patient affected with pain comprising co-administering said rofecoxib and/or at least one pharmaceutically acceptable salt thereof with an effective amount of oxycodone and/or at least one pharmaceutically acceptable salt thereof, to augment the analgesia attributable to said rofecoxib and/or at least one pharmaceutically acceptable salt thereof during at least a portion of the dosage interval of said rofecoxib and/or at least one pharmaceutically acceptable salt thereof.

* * * * *

UNITED STATES PATENT AND TRADEMARK OFFICE
CERTIFICATE OF CORRECTION

PATENT NO.   : 6,552,031 B1
DATED        : April 22, 2003
INVENTOR(S)  : Burch et al.

It is certified that error appears in the above-identified patent and that said Letters Patent is hereby corrected as shown below:

Title page,
Item [54], Title, reads "SYNERGISTIC ANALGESIC COMBINATION OF OXYCODONE AND ROFECOXIB" and should read -- ANALGESIC COMBINATION OF OXYCODONE AND ROFECOXIB --.

Signed and Sealed this

Fourteenth Day of February, 2006

JON W. DUDAS
*Director of the United States Patent and Trademark Office*